US010667680B2

(12) United States Patent
Gupta et al.

(10) Patent No.: US 10,667,680 B2
(45) Date of Patent: Jun. 2, 2020

(54) FORECASTING EYE CONDITION PROGRESSION FOR EYE PATIENTS

(71) Applicant: Microsoft Technology Licensing, LLC, Redmond, WA (US)

(72) Inventors: Manish Gupta, Hyderabad (IN); Prashant Gupta, Hyderabad (IN); Joy Mustafi, Hyderabad (IN)

(73) Assignee: Microsoft Technology Licensing, LLC, Redmond, WA (US)

( * ) Notice: Subject to any disclaimer, the term of this patent is extended or adjusted under 35 U.S.C. 154(b) by 421 days.

(21) Appl. No.: 15/418,667

(22) Filed: Jan. 27, 2017

(65) Prior Publication Data
US 2018/0160894 A1   Jun. 14, 2018

(30) Foreign Application Priority Data

Dec. 9, 2016   (IN) .............................. 201641042225

(51) Int. Cl.
*A61B 5/00*   (2006.01)
*A61B 3/00*   (2006.01)
(Continued)

(52) U.S. Cl.
CPC ............ *A61B 3/0025* (2013.01); *A61B 3/028* (2013.01); *A61B 3/107* (2013.01); *A61B 5/4842* (2013.01); *A61B 5/7264* (2013.01); *A61B 5/7275* (2013.01); *G16H 20/10* (2018.01); *G16H 50/50* (2018.01)

(58) Field of Classification Search
CPC ..... A61B 3/0025; A61B 3/028; A61B 5/4842; A61B 5/7275; A61B 3/107; A61B 34/10; G16H 50/50
See application file for complete search history.

(56) References Cited

U.S. PATENT DOCUMENTS 4,420,228 A  * 12/1983  Humphrey ............. A61B 3/107
                                                351/212
6,496,827 B2   12/2002  Kozam et al.
(Continued)

OTHER PUBLICATIONS

Gupta, et al, "Predicting Post-Operative Visual Acuity for Lasik Surgeries", In Proceedings of Pacific-Asia Conference on Knowledge Discovery and Data Mining, Apr. 2016, pp. 1-12.
(Continued)

*Primary Examiner* — Max F Hindenburg
(74) *Attorney, Agent, or Firm* — Ray Quinney & Nebeker; Thomas M. Hardman; Daniel Choi

(57) ABSTRACT

Aspects extend to methods, systems, and computer program products for forecasting eye condition progression for eye patients. When a patient visits an eye practitioner, the patient (or when appropriate their guardian) may be interested in the current eye condition as well as a prediction of eye condition progression in the future and/or as the patient ages. Aspects of the invention can be used to predict the progress of an eye condition for a patient (e.g., a child) at a number of different post-examination times after an examination. Predicting the progress of an eye condition for a patient over time can be used to assist the eye practitioner in tailoring a treatment plan and/or tailoring a subsequent examination schedule for the patient.

17 Claims, 7 Drawing Sheets

(51) Int. Cl.
   *A61B 3/107*   (2006.01)
   *A61B 3/028*   (2006.01)
   *G16H 50/50*   (2018.01)
   *G16H 20/10*   (2018.01)

(56) References Cited

U.S. PATENT DOCUMENTS

| | | | |
|---|---|---|---|
| 6,626,538 | B1 | 9/2003 | Arrowsmith |
| 7,520,611 | B2 | 4/2009 | Franz et al. |
| 7,607,776 | B1 | 10/2009 | Lewis et al. |
| 7,789,513 | B2 | 9/2010 | Pettit et al. |
| 7,954,950 | B2* | 6/2011 | Dreher ............ B29D 11/00413 351/246 |
| 8,061,843 | B2 | 11/2011 | Kline |
| 8,486,054 | B2* | 7/2013 | Bischoff ............ G06F 19/3481 606/4 |
| 9,230,062 | B2 | 1/2016 | Seriani |
| 9,307,904 | B2 | 4/2016 | Padrick et al. |
| 2002/0052551 | A1 | 5/2002 | Sinclair et al. |
| 2004/0054358 | A1 | 3/2004 | Cox et al. |
| 2012/0245484 | A1 | 9/2012 | McClatchey et al. |
| 2014/0320805 | A1 | 10/2014 | Wilzbach et al. |
| 2015/0103313 | A1 | 4/2015 | Sarver et al. |
| 2015/0324974 | A1 | 11/2015 | Garber et al. |
| 2016/0100752 | A1 | 4/2016 | Mchugh et al. |
| 2016/0128892 | A1 | 5/2016 | Nimtsovitch |
| 2016/0174830 | A1 | 6/2016 | Rubin et al. |

OTHER PUBLICATIONS

Gallagher, et al., "Paediatric intraocular lens implants: accuracy of lens power calculations", In Journal of Eye, vol. 30, No. 9, Sep. 2016, 2 pages.

Caldwell, Emily, "One test can predict which kids will become nearsighted", https://news.osu.edu/news/2015/04/02/%E2%80%8Bone-test-can-predict-which-kids-will-become-nearsighted/, Apr. 2, 2015, 4 pages.

Fang, et al., "Advanced Intraocular Lens Power Calculations", In Publication of Springer Berlin Heidelberg, Retrieved on: Sep. 21, 2016, pp. 31-46.

Fan, et al., "Hierarchical Graph-Coupled HMMs for Heterogeneous Personalized Health Data", In Proceedings of 21stACM SIGKDD International Conference on Knowledge Discovery and Data Mining, Aug. 10, 2015, pp. 239-248.

Che, et al., "Deep Computational Phenotyping", In Proceedings of 21st ACM SIGKDD International Conference on Knowledge Discovery and Data Mining, Aug. 10, 2015, 507-516 pages.

Liu, et al., "Temporal Phenotyping from Longitudinal Electronic Health Records: A Graph Based Framework", In Proceedings of 21st ACM SIGKDD International Conference on Knowledge Discovery and Data Mining, Aug. 10, 2015, 705-714 pages.

Ho, et al., "Marble: High-throughput Phenotyping from Electronic Health Records via Sparse Nonnegative Tensor Factorization", In Proceedings of 20th ACM SIGKDD International Conference on Knowledge Discovery and Data Mining, Aug. 24, 2014, 115-124 pages.

Caballero, et al., "Dynamically Modeling Patient's Health State from Electronic Medical Records: A Time Series Approach", In Proceedings of 21st ACM SIGKDD International Conference on Knowledge Discovery and Data Mining, Aug. 10, 2015, 69-78 pages.

Somanchi, et al., "Early Prediction of Cardiac Arrest (Code Blue) using Electronic Medical Records", In Proceedings of 21st ACM SIGKDD International Conference on Knowledge Discovery and Data Mining, Aug. 11, 2015, pp. 2119-2126.

Ghassemi, et al., "Unfolding Physiological State: Mortality Modelling in Intensive Care Units", In Proceedings of 20th ACM SIGKDD International Conference on Knowledge Discovery and Data Mining, Aug. 24, 2014, pp. 75-84.

Nori, et al., "Simultaneous Modeling of Multiple Diseases for Mortality Prediction in Acute Hospital Care", In Proceedings of 21st ACM SIGKDD International Conference on Knowledge Discovery and Data Mining, Aug. 10, 2015, 855-864 pages.

Caruana, et al., "Intelligible Models for HealthCare: Predicting Pneumonia Risk and Hospital 30-day Readmission", In Proceedings of 21st ACM SIGKDD International Conference on Knowledge Discovery and Data Mining, Aug. 10, 2015, 1721-1730 pages.

Roy, et al., "Dynamic Hierarchical Classification for Patient Risk-of-Readmission", In Proceedings of 21st ACM SIGKDD International Conference on Knowledge Discovery and Data Mining, Aug. 10, 2015, 1691-1700 pages.

* cited by examiner

301 — ACCESSING EYE CHARACTERISTIC DATA FOR THE PATIENT'S EYES, THE EYE CHARACTERISTIC DATA ACQUIRED DURING AN EYE EXAMINATION PERFORMED ON THE PATIENT, THE EYE CHARACTERISTIC DATA INCLUDING ONE OR MORE MEASURED SPHERE VALUES FOR THE SPHERE OF THE PATIENT'S EYES

302 — ACCESSING DEMOGRAPHIC DATA FOR THE PATIENT

303 — INPUTTING THE EYE CHARACTERISTIC DATA, INCLUDING THE ONE OR MORE MEASURED SPHERE VALUES FOR THE SPHERE OF THE PATIENT'S EYES, AND THE DEMOGRAPHIC DATA INTO A PREDICTIVE MODEL IN THE SYSTEM MEMORY, THE PREDICTIVE MODEL FORMULATED FROM OTHER PATIENT DATA ACQUIRED DURING OTHER EYE EXAMINATIONS FOR A PLURALITY OF OTHER PATIENTS, THE OTHER PATIENT DATA INCLUDING, FOR EACH OTHER PATIENT INCLUDED IN THE PLURALITY OF OTHER PATIENTS, ONE OR MORE MEASURED SPHERE VALUES FOR THE SPHERE OF THE OTHER PATIENT'S EYES, OTHER EYE CHARACTERISTIC DATA FOR THE OTHER PATIENT'S EYES, AND DEMOGRAPHIC DATA FOR THE OTHER PATIENT, THE PREDICTIVE MODEL TRANSFORMING THE EYE CHARACTERISTIC DATA FOR THE PATIENT, THE DEMOGRAPHIC DATA FOR THE PATIENT, AND THE OTHER PATIENT DATA THROUGH LINEAR REGRESSION INCLUDING:

304 — FORECASTING SPHERE VALUES FOR THE SPHERE OF THE PATIENT'S EYES AT A PLURALITY OF DIFFERENT POST EXAMINATION TIME PERIODS, THE FORECAST SPHERE VALUES INFERRED FROM THE EYE CHARACTERISTIC DATA FOR THE PATIENT, INCLUDING THE ONE OR MORE MEASURED SPHERE VALUES FOR THE SPHERE OF THE PATIENT'S EYES, AND THE DEMOGRAPHIC DATA FOR THE PATIENT IN VIEW OF THE OTHER PATIENT DATA; AND

305 — FORMULATING A TIME SERIES CHART OF SPHERE FOR THE PATIENT'S EYES FROM THE FORECAST SPHERE VALUES, THE TIME SERIES CHART FORECASTING LIKELY SPHERE VALUES FOR THE SPHERE OF THE PATIENT'S EYES OVER A PLURALITY OF DIFFERENT TIME PERIODS IN THE FUTURE

306 — RETURNING THE FORMULATED TIME SERIES CHART AS A PREDICTION OF CHANGES TO THE SPHERE OF THE PATIENT'S EYES AS THE PATIENT AGES

*FIG. 3*

501 ACCESSING EYE CHARACTERISTIC DATA FOR THE PATIENT'S EYES, THE EYE CHARACTERISTIC DATA ACQUIRED DURING A PLURALITY OF DIFFERENT EYE EXAMINATIONS PERFORMED ON THE PATIENT, EACH EYE EXAMINATION INCLUDED IN THE PLURALITY OF DIFFERENT EYE EXAMINATIONS PERFORMED AT A DIFFERENT TIME AND SEPARATED FROM A NEXT SUBSEQUENT EYE EXAM INCLUDED IN THE PLURALITY OF EYE DIFFERENT EYE EXAMINATIONS BY A TIME GAP, FOR EACH OF THE PLURALITY OF DIFFERENT EYE EXAMINATIONS, THE EYE CHARACTERISTIC DATA INCLUDING ONE OR MORE MEASURED SPHERE VALUES FOR THE SPHERE OF THE PATIENT'S EYES

502 ACCESSING DEMOGRAPHIC DATA FOR THE PATIENT

503 INPUTTING THE EYE CHARACTERISTIC DATA, TIME GAPS, AND DEMOGRAPHIC DATA INTO A PREDICTIVE MODEL, THE EYE CHARACTERISTIC DATA INCLUDING, FOR EACH OF THE PLURALITY OF DIFFERENT EYE EXAMINATIONS, THE ONE OR MORE MEASURED SPHERE VALUES FOR THE SPHERE OF THE PATIENT'S EYES, THE PREDICTIVE MODEL FORMULATED FROM OTHER PATIENT DATA ACQUIRED DURING OTHER EYE EXAMINATIONS FOR A PLURALITY OF OTHER PATIENTS, THE OTHER PATIENT DATA INCLUDING, FOR EACH OTHER PATIENT INCLUDED IN THE PLURALITY OF OTHER PATIENTS, ONE OR MORE MEASURED SPHERE VALUES FOR THE SPHERE OF THE OTHER PATIENT'S EYES, OTHER EYE CHARACTERISTIC DATA FOR THE OTHER PATIENT'S EYES, AND DEMOGRAPHIC DATA FOR THE OTHER PATIENT, THE PREDICTIVE MODEL TRANSFORMING THE EYE CHARACTERISTIC DATA FOR THE PATIENT, THE TIME GAPS, AND THE DEMOGRAPHIC DATA FOR THE PATIENT THROUGH LINEAR REGRESSION INCLUDING:

504 FORECASTING SPHERE VALUES FOR THE SPHERE OF THE PATIENT'S EYES AT A PLURALITY OF DIFFERENT POST EXAMINATION TIME PERIODS, THE FORECAST SPHERE VALUES INFERRED FROM THE ONE OR MORE MEASURED SPHERE VALUES FOR THE SPHERE OF THE PATIENT'S EYES ACQUIRED DURING DIFFERENT EYE EXAMINATIONS FOR THE PATIENT AND FROM THE DEMOGRAPHIC DATA FOR THE PATIENT IN VIEW OF THE TIME GAPS SEPARATING EACH OF THE PLURALITY OF EYE EXAMINATIONS

505 FORMULATING A TIME SERIES CHART OF SPHERE FOR THE PATIENT'S EYES FROM THE FORECAST SPHERE VALUES, THE TIME SERIES CHART FORECASTING LIKELY SPHERE VALUES FOR THE SPHERE OF THE PATIENT'S EYES OVER A PLURALITY OF DIFFERENT TIME PERIODS IN THE FUTURE

506 RETURNING THE FORMULATED TIME SERIES CHART AS A PREDICTION OF CHANGES TO THE SPHERE OF THE PATIENT'S EYES AS THE PATIENT AGES

*FIG. 5*

FORECASTING EYE CONDITION PROGRESSION FOR EYE PATIENTS

CROSS-REFERENCE TO RELATED APPLICATIONS

This application claims priority to Indian National Application No. 201641042225, filed Dec. 9, 2016, and entitled "FORECASTING EYE CONDITION PROGRESSION FOR EYE PATIENTS"

BACKGROUND

1. Background and Relevant Art

Part of general health is eye health. From time to time, for example, once a year, an eye patient can visit an eye practitioner (e.g., an optometrist or ophthalmologist) for an eye examination. The eye practitioner can measure various eye characteristics and perform various eye tests to determine general eye health. Eye characteristics can change over time, especially with age. Thus, eye patients can return to an eye practitioner on an ongoing basis to check for changes in eye characteristics.

However, some eye patients are unable to regularly visit an eye practitioner (e.g., due to location, financial resources, etc.). Other eye patients may frequently change eye practitioners, for example, due to moving between different geographic locations. Further eye patients may visit an eye practitioner to frequently, receiving redundant eye examinations even though their eye characteristics have not clinically changed.

These types of irregular or redundant eye practitioner visits are especially problematic in pediatric settings. Parents of a child are typically very eager to know not just the current condition of their child's eyes but also a treatment plan for any corrections and when those corrections may occur. Unfortunately, it is difficult to take the current eye condition as an input and determine a timed treatment plan with desired outcomes.

BRIEF SUMMARY

Examples extend to methods, systems, and computer program products for forecasting eye condition progression for eye patients. A computer system accesses eye characteristic data for a patient's eyes. The eye characteristic data was acquired during one or more eye examinations performed on the patient. In some aspects, the eye characteristic data was acquired during a plurality of different eye examinations performed on the patient. Each of the plurality of different eye examinations was performed at a different time and separated from a next subsequent eye exam included in the plurality of eye different eye examinations by a time gap.

The eye characteristic data includes one or more measured condition values for an eye condition of the patient's eyes from each eye examination. A condition value can be a value for essentially any eye condition, such as, for example, sphere, cylinder, a condition with a sphere component and a cylinder component, a condition based on other eye characteristics, an eye disease, etc. In one aspect, data is sent directly from one or more diagnostic devices that measure eye characteristics to the computer system. The computer system accesses demographic data for the patient.

The computer system inputs the eye characteristic data, including the one or more measured condition values for the eye condition of the patient's eyes, the demographic data, and, when appropriate any time gaps, into a predictive model in system memory. The predictive model having been formulated from other patient data acquired during other eye examinations for a plurality of other patients. The other patient data includes, for each other patient included in the plurality of other patients, one or more measured condition values for the eye condition of the other patient's eyes, other eye characteristic data for the other patient's eyes, and demographic data for the other patient.

In one aspect, the predictive model transforms the eye characteristic data for the patient, the demographic data for the patient, and the other patient data through linear regression. Using linear regression, the predictive model forecasts condition values for the sphere of the patient's eyes at a plurality of different post examination time periods. The forecast condition values are inferred from the eye characteristic data for the patient, including the one or more measured condition values for the sphere of the patient's eyes, and the demographic data for the patient in view of the other patient data.

In another aspect, the predictive model transforms the eye characteristic data for the patient, time gaps, and the demographic data for the patient through linear regression. Using linear regression, the predictive model forecasts condition values for the sphere of the patient's eyes at a plurality of different post examination time periods. The forecast condition values are inferred from the one or more measured condition values for the sphere of the patient's eyes acquired during different eye examinations for the patient and from the demographic data for the patient in view of the time gaps separating each of the plurality of eye examinations.

The computer system formulates a time series chart of the eye condition for the patient's eyes from the forecast condition values. The time series chart forecasts likely condition values for the eye condition of the patient's eyes over a plurality of different time periods in the future. The predictive model returns the formulated time series chart as a prediction of changes to the eye condition for the patient's eyes as the patient ages.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by practice. The features and advantages may be realized and obtained by means of the instruments and combinations particularly pointed out in the appended claims. These and other features and advantages will become more fully apparent from the following description and appended claims, or may be learned by practice as set forth hereinafter.

BRIEF DESCRIPTION OF THE DRAWINGS

In order to describe the manner in which the above-recited and other advantages and features can be obtained, a more particular description will be rendered by reference to specific implementations thereof which are illustrated in the appended drawings. Understanding that these drawings depict only some implementations and are not therefore to be considered to be limiting of its scope, implementations will be described and explained with additional specificity and detail through the use of the accompanying drawings in which:

FIG. 3 illustrates a flow chart of an example method for providing forecasting sphere values for an eye patient.

FIG. 5 illustrates a flow chart of an example method for forecasting sphere values for an eye patient.

DETAILED DESCRIPTION

Figure 1:
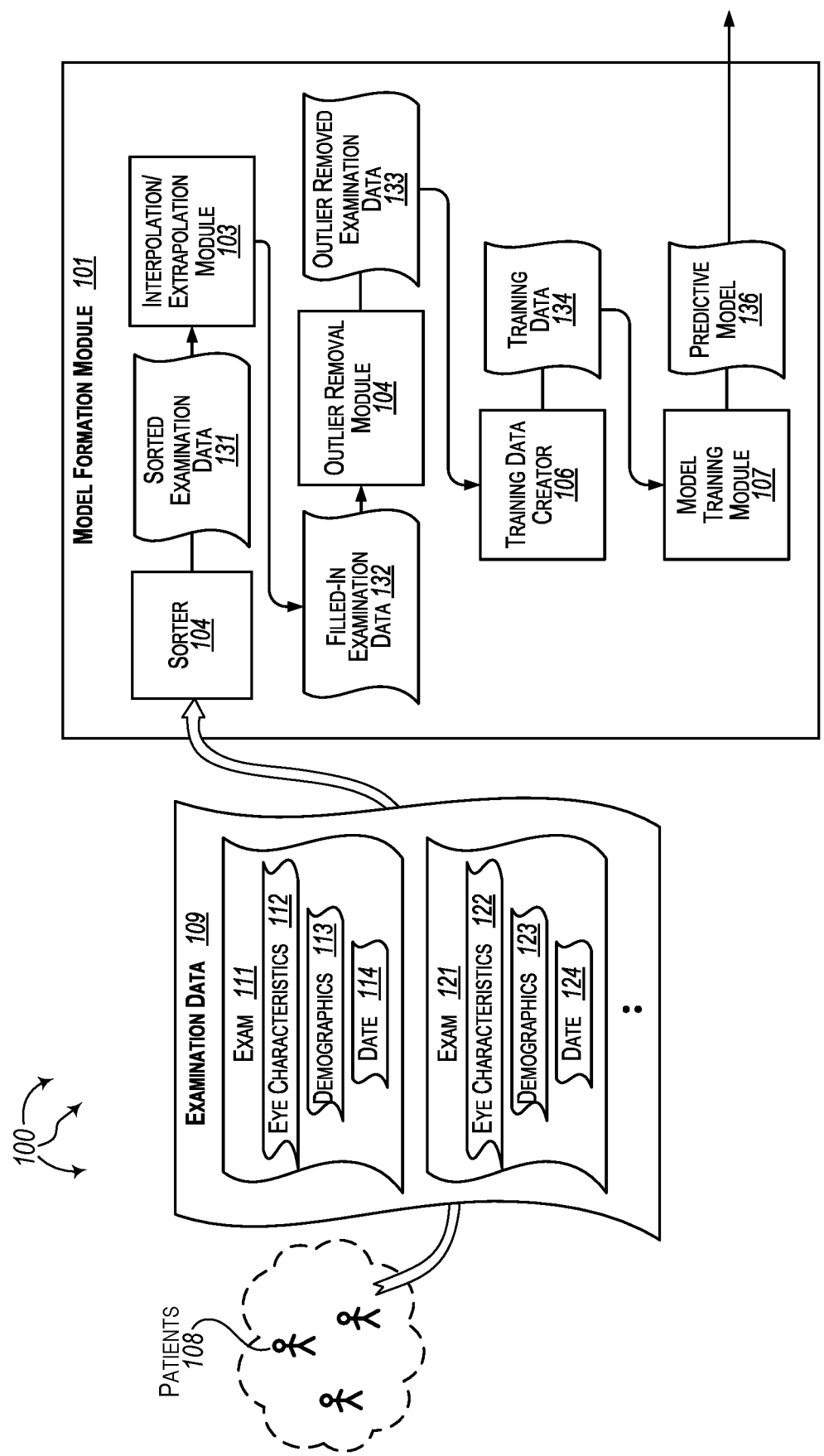
FIG. 1 illustrates an example computer architecture that facilitates formulating and training a predictive model to forecast the progression of eye conditions for eye patients.

Examples extend to methods, systems, and computer program products for forecasting eye condition progression for eye patients. A computer system accesses eye characteristic data for a patient's eyes. The eye characteristic data was acquired during an eye examination performed on the patient. The eye characteristic data includes one or more measured condition values for an eye condition of the patient's eyes. A condition value can be a value for essentially any eye condition, such as, for example, sphere, cylinder, a condition with a sphere component and a cylinder component, a condition based on other eye characteristics, an eye disease, etc. In one aspect, data is sent directly from one or more diagnostic devices that measure eye characteristics to the computer system. The computer system access demographic data for the patient.

The computer system inputs the eye characteristic data, including the one or more measured condition values for the eye condition of the patient's eyes, and the demographic data into a predictive model in system memory. The predictive model having been formulated from other patient data acquired during other eye examinations for a plurality of other patients. The other patient data includes, for each other patient included in the plurality of other patients, one or more measured condition values for the eye condition of the other patient's eyes, other eye characteristic data for the other patient's eyes, and demographic data for the other patient.

The predictive model transforms the eye characteristic data for the patient, the demographic data for the patient, and the other patient data through linear regression. Using linear regression, the predictive model forecasts condition values for the eye condition of the patient's eyes at a plurality of different post examination time periods. The forecast condition values are inferred from the eye characteristic data, including the one or more measured condition values for the sphere of the patient's eyes, and the demographic data in view of the other patient data.

The predictive model formulates a time series chart of the eye condition for the patient's eyes from the forecast condition values. The time series chart forecasts likely condition values for the eye condition of the patient's eyes over a plurality of different time periods in the future. The predictive model returns the formulated time series chart as a prediction of changes to the eye condition for the patient's eyes as the patient ages.

In other aspects, a computer system accesses eye characteristic data for the patient's eyes. The eye characteristic data was acquired during a plurality of different eye examinations performed on the patient. Each eye examination, included in the plurality of different eye examinations, was performed at a different time and separated from a next subsequent eye exam included in the plurality of eye different eye examinations by a time gap. For each of the plurality of different eye examinations, the eye characteristic data includes one or more measured condition values for an eye condition of the patient's eyes. The computer system access demographic data for the patient.

The computer system inputs the eye characteristic data, time gaps, and demographic data into a predictive model. The eye characteristic data includes, for each of the plurality of different eye examinations, the one or more measured condition values for the eye condition of the patient's eyes. The predictive model having been formulated from other patient data acquired during other eye examinations for a plurality of other patients. The other patient data includes, for each other patient included in the plurality of other patients, one or more measured condition values for the eye condition of the other patient's eyes, other eye characteristic data for the other patient's eyes, and demographic data for the other patient The predictive model transforms the eye characteristic data for the patient, the time gaps, and the demographic data for the patient through linear regression. Using linear regression, the predictive model forecasts condition values for the eye condition of the patient's eyes at a plurality of different post examination time periods. The forecast condition values are inferred from the one or more measured condition values for the eye condition of the patient's eyes acquired during different eye examiners for the patient and from the demographic data for the patient in view of the time gaps separating each of the plurality of eye examinations.

The predictive model formulates a time series chart of eye condition for the patient's eyes from the forecast condition values. The time series chart forecasts likely condition values for the eye condition of the patient's eyes over a plurality of different time periods in the future. The computer system returns the formulated time series chart as a prediction of changes to the eye condition for the patient's eyes as the patient ages.

Implementations may comprise or utilize a special purpose or general-purpose computer including computer hardware, such as, for example, one or more computer and/or hardware processors (including Central Processing Units (CPUs) and/or Graphical Processing Units (GPUs)) and system memory. Some computer systems can include and/or be (e.g., network) connected to eye examination devices for examining and/or mapping the human eye. Other devices are also discussed in greater detail below.

Implementations also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations can comprise at least two distinctly different kinds of computer-readable media: computer storage media (devices) and transmission media.

Computer storage media (devices) includes RAM, ROM, EEPROM, CD-ROM, Solid State Drives ("SSDs") (e.g., RAM-based or Flash-based), Shingled Magnetic Recording ("SMR") devices, Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

In one aspect, one or more processors are configured to execute instructions (e.g., computer-readable instructions, computer-executable instructions, etc.) to perform any of a plurality of described operations. The one or more processors can access information from system memory and/or store information in system memory. The one or more processors can (e.g., automatically) transform information between different formats, such as, for example, between any of: eye examination data, eye characteristics, eye characteristic data, demographic data, dates, sorted examination data, filled-in examination data, outlier removed examination data, training data, predictive models, sphere values, eye conditions, condition values, times, time series charts, time gaps, tailored treatment recommendations, tailored examination schedule, etc.

System memory can be coupled to the one or more processors and can store instructions (e.g., computer-readable instructions, computer-executable instructions, etc.) executed by the one or more processors. The system memory can also be configured to store any of a plurality of other types of data generated and/or transformed by the described components, such as, for example, eye examination data, eye characteristics, eye characteristic data, demographic data, dates, sorted examination data, filled-in examination data, outlier removed examination data, training data, predictive models, sphere values, eye conditions, condition values, times, time series charts, time gaps, tailored treatment recommendations, tailored examination schedules, etc.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, in response to execution at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the described aspects may be practiced in network computing environments with many types of computer system configurations, including, personal computers, desktop computers, laptop computers, message processors, hand-held devices, wearable devices, multicore processor systems, multi-processor systems, microprocessor-based or programmable consumer electronics, network PCs, minicomputers, mainframe computers, mobile telephones, PDAs, tablets, routers, switches, and the like. The described aspects may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. In another example, computer code is configured for execution in one or more processors, and may include hardware logic/electrical circuitry controlled by the computer code. These example devices are provided herein purposes of illustration, and are not intended to be limiting. Embodiments of the present disclosure may be implemented in further types of devices.

The described aspects can also be implemented in cloud computing environments. In this description and the following claims, "cloud computing" is defined as a model for enabling on-demand network access to a shared pool of configurable computing resources. For example, cloud computing can be employed in the marketplace to offer ubiquitous and convenient on-demand access to the shared pool of configurable computing resources (e.g., compute resources, networking resources, and storage resources). The shared pool of configurable computing resources can be provisioned via virtualization and released with low effort or service provider interaction, and then scaled accordingly.

A cloud computing model can be composed of various characteristics such as, for example, on-demand self-service, broad network access, resource pooling, rapid elasticity, measured service, and so forth. A cloud computing model can also expose various service models, such as, for example, Software as a Service ("SaaS"), Platform as a Service ("PaaS"), and Infrastructure as a Service ("IaaS"). A cloud computing model can also be deployed using different deployment models such as private cloud, community cloud, public cloud, hybrid cloud, and so forth. In this description and in the following claims, a "cloud computing environment" is an environment in which cloud computing is employed.

In this description and the following claims, "linear regression" is defined as an approach for modeling the relationship between a scalar dependent variable y and one or more explanatory variables (or independent variables) denoted X. Linear regression for one explanatory variable can be referred to as simple linear regression. Linear regression for multiple explanatory variables can be referred to as multiple linear regression.

In linear regression, relationships can be modeled using linear predictor models whose unknown model parameters are estimated from the data. For example, the conditional mean of y given the value of X is assumed to be an affine function of X. Less commonly, the median or some other quantile of the conditional distribution of y given X is expressed as a linear function of X. Similar to other regression analysis, linear regression can focuses on the conditional probability distribution of y given X, rather than on the joint probability distribution of y and X (which is instead the domain of multivariate analysis.)

Linear regression has a variety of uses. Linear regression can be used for prediction, forecasting, or error reductions. For example, linear regression can be used to fit a predictive model to an observed data set of y and X values. After developing such a model, if an additional value of X is then given without its accompanying value of y, the fitted model can be used to make a prediction of the value of y.

Linear regression models can include FastTree regression, FastRank (boosted decision trees) regression, Poisson regression, gradient tree bosting regression, online gradient descent based regression, and neural network based regression.

In this description and in the following claims, "sphere" is defined as the correction for nearsightedness or farsightedness being "spherical," or equal in all meridians of the eye. Sphere can indicate the amount of lens power (e.g., measured in diopters) prescribed to correct nearsightedness or farsightedness. A minus sign ('−') can be used to indicate correction of nearsightedness. A plus sign ('+') or no sign can be used to indicate correction of farsightedness.

In this description and in the following claims, "cylinder" is defined as the correction for astigmatism being not spherical. Instead the correction is shaped so one meridian has no added curvature, and the meridian perpendicular to this "no added power" meridian contains the maximum power and lens curvature to correct astigmatism. Cylinder can indicate the amount of lens power to correct astigmatism. A minus sign ('−') can be used to indicate correction of nearsighted astigmatism. A plus sign ('+') can be used to indicate correction of farsighted astigmatism.

In this description and in the following claims, "axis" is defined as orientation of the axis of the cylindrical lens. The direction of the axis is measured in degrees anticlockwise from a horizontal line drawn through the center of a pupil (the axis number can be different for each eye) when viewed from the front side of the glasses (i.e., when viewed from the point of view of the person making the measurement). It varies from 1 to 180 degrees.

In this description and in the following claims, "visual acuity" (or "VA") is defined as clarity of vision. Visual acuity is a measure of the spatial resolution of the visual processing system.

In this description and the following claims, "uncorrected visual acuity (or "UCVA") is defined as visual acuity without corrective lenses.

In this description and in the following claims, "best corrected visual acuity (or "BCVA") is defined best achievable visual acuity with corrective lenses (e.g., glasses or contacts).

In this description and in the following claims, "OD" represents an abbreviation for oculus dexter, which is latin for right eye.

In this description and in the following claims, "OS" represents an abbreviation for oculus sinister, which is latin for left eye.

When a patient visits an eye practitioner (e.g., an optometrist or ophthalmologist), the patient (or when appropriate their guardian) may be interested in a current eye condition as well as a prediction for the eye condition at one or more time future times. Aspects of the invention can be used to predict the progression of an eye condition for a patient (e.g., a child) at a number of different post-examination times, such as, for example, 6 months, 1 year, 2 years, etc. after an examination.

Predicting an eye condition progression for a patient over time can be used to assist the eye practitioner in tailoring a treatment plan and/or tailoring a subsequent examination schedule for the patient. For example, if sphere is predicted to go very high, the eye practitioner can recommend special care in terms of specific treatment or diet change or habit changes.

In general, the current condition of the eye can be used as input to a predictive model. The predictive model can use linear regression to output a forecasted time series of predicted progression of the eye condition (e.g., sphere, cylinder, etc.) over a subsequent period of time (e.g., months or years). The predictive model can be accessed and/or implemented as a Web API, as an app on the web, through a SaaS offering, or on mobiles or any other platform.

It can be challenging to take the current eye condition as an input, and display a forecasted time series of a predicted eye condition. Large sequential examination data over multiple years for the same patient is often not readily available. Further, examination data can be sparse (i.e., there can be of missing values) and can also include a potentially large number of outlier entries.

Nonetheless, a predictive model can be formulated from and trained on eye characteristic data and demographic data acquired from previously conducted eye examinations for a plurality of other eye patients. The eye characteristic data can be acquired from multiple eye examinations for at least some of the plurality of other eye patients. For example, eye characteristics data can be acquired from hundreds of thousands of examinations given to tens of thousands of eye patients.

For each examination, eye characteristic data can include measured values for any (and potentially all) of: UCVA for one or both eyes, BCVA for one or both eyes, sphere for one or both eyes, axis for one or both eyes, and cylinder for one or both eyes, any eye diseases, etc. Demographic data can include any (and potentially all) of patient ID, age, gender, city, district, state, etc. Each examination can be uniquely identified by the patent ID and examination date.

Based at last in part on data set size, a predictive model can be trained in a manner that compensates for lack of multiple entries for some patients and compensates for missing values within data for individual eye examinations. Data can be sorted by patient ID and then by visit date. For each patient's data, outliers are identified and removed. Outliers can include values that are inappropriately high (e.g., sphere value>16) or that change at an in appropriately high rate over time (e.g., a change of 0.5 or more per month for a sphere value).

After removing outliers, training data instances are created. For any two examinations for a patient, all measured values (for each eye) for a first examination and the gap in months between the first and second visit are considered. A (e.g., sphere, cylinder, axis, etc.) value (for each eye) for the second examination is used as the label. As such, there can two labels per instances of training data, a (e.g., sphere, cylinder, axis, eye disease, etc.) value for the left eye and a (e.g., sphere, cylinder, axis, eye disease, etc.) value for the right eye.

FIG. 1 illustrates an example computer architecture 100 that facilitates formulating and training a predictive model to forecast the progression of eye conditions for eye patients. Referring to FIG. 1, computer architecture 100 includes model formulation module 101 and patients 108. Model formulation module 101 and information technology resources storing examination data for patients 108 can be connected to (or be part of) a network, such as, for example, a system bus, a Local Area Network ("LAN"), a Wide Area Network ("WAN"), and even the Internet. Accordingly, model formulation module 101 and information technology resources storing examination data for patients 108 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Model formulation module 101 further includes sorter 102, interpolation/extrapolation module 103, outlier removal module 104, training data creator 106, and model training module 107. Sorter 102 is configured to sort examination data by patient ID and date. Interpolation/extrapolation module 103 is configured to filled in missing values in sorted examination data. Outlier removal module 104 is configured to remove outlier values from filled-in examination data. Training data creator 106 is configured to generated training data from outlier removed examination data. Model training module 107 is configured to train and formulate predictive models from training data.

Each of patients 108 can undergo one or more eye examinations at different times. The eye examinations can be performed by an eye practitioner or by a plurality of different eye practitioners. Examination data from each eye examination can be stored on information technology resources, for example, at an eye practitioner's office, in a cloud, etc.

Appropriate health care and/or privacy regulations (depending on country) can be followed to collect the examination data for each eye examination. The collected examination data can be combined into examination data 109. Examination data 109 can include demographic data. However, any personally identifiable information for eye patients can be omitted from examination data 109. Examination data 109 may be stored at a storage device (e.g., locally, on cloud resources, etc.) under control of an entity that creates predictive models. Examination data 109 can be stored in accordance with appropriate health care and/or privacy regulations.

More specifically, examination data 109 includes, for each eye examination, eye characteristics and demographics for an eye patient and a date the eye examination was conducted. For example, examination data 109 includes exam 111, exam 121, etc. Exam 111 includes eye characteristics 112, demographics 113, and date 114. Similarly, exam 121 includes eye characteristics 122, demographics 123, and date 124.

Eye characteristics for an eye examination can include one or more measured values for different eye characteristics for a patient. The different eye characteristics can include but are not limited to values for: right eye cylinder (od_cyl), right eye axis (od_axis), right eye UCVA (od_ucva), right eye BCVA (od_bcva), right eye sphere (od_sph), left eye cylinder (os_cyl), left eye axis (os_axis), left eye UCVA (os_ucva), left eye BCVA (os_bcva), left eye sphere (os_sph), and any eye diseases. Demographic data can include one or more recorded values for different demographic characteristics for a patient. The different demographic characteristics can include but are not limited to values for: patient ID, age, gender, city, district, state, etc.

Model formulation module 101 can access examination data 109. Model formulation module 101 can use examination data 109 to formulate predictive model 136. Predictive model 136 can be a model for predicting (forecasting) changes in an eye condition (e.g., sphere, cylinder, a condition with a sphere component and a cylinder component, an eye disease, etc.) for eye patients over time.

Examination data 109 can be initially received at sorter 102. Sorter 102 can sort examination data 109 by patient ID and date. Sorter 102 can output sorted examination 131. Sorted examination data 131 is examination data 109 sorted by patient ID and date. Interpolation/Extrapolation module 103 receives sorted examination data 131 as input. Interpolation/Extrapolation module 103 interpolates and/or extrapolates missing values in examination data 109.

Interpolation/Extrapolation module 103 can use values from one or more examinations for a patient to interpolate and/or extrapolate missing values in one or more other examinations for the patient. For example, it may be that a patient had eye examinations on Mar. 4, 2013, Mar. 1, 2014, and Mar. 8, 2015. In one data pattern, an od_sph value of 1.5 was recorded for the Mar. 4, 2013 examination, no od_sph value was recorded for the Mar. 1, 2014 examination, and an od_sph value of 2.0 was recorded for the Mar. 8, 2015 examination. Interpolation/Extrapolation module 103 can interpolate the od_sph value from the Mar. 1, 2014 examination to be 1.75.

In another data pattern, an od_cyl value of 1.5 was recorded for the Mar. 4, 2013 examination, an od_cyl value of 2.0 was recorded for the Mar. 1, 2014 examination, and no od_cyl value was recorded for the Mar. 8, 2015 examination. Interpolation/Extrapolation module 103 can extrapolate the od_cyl value from the Mar. 8, 2015 examination to be 2.0.

Interpolation/Extrapolation module 103 can also use values for one or more patients to interpolate and/or extrapolate missing values for another patient. When available examination data is limited for a patient, for example, due to number of examinations (e.g., one examination) or due to missing values within examinations, interpolation/extrapolation module 103 can refer to examination data of other patients with similar eye characteristics and demographics. A requisite correlation of eye characteristics between a patient and another patient can include the patient having values for one or more eye characteristics within a specified range of values for the one or more eye characteristics for the other patient within a specified time range. Values for the one or more other eye characteristics for the other patient within with a specified time range can be interpolated/extrapolated from values for one or more other eye characteristics recorded at other times For example, it may be that a first patient had eye examinations on Jun. 7, 2013, and Jul. 12, 2015. An os_sph value of 1.25 was recorded for the Jun. 7, 2013 examination and an os_sph value of 1.75 was recorded for the Jul. 12, 2015 examination. A second patient having a requisite correlation of eye characteristics to the patient and of similar age and gender may have had an eye examination on Jun. 24, 2014. However, no os_sph value was recorded for the Jun. 24, 2014 examination.

Interpolation/extrapolation module 103 can interpolate an approximate value for os_sph and values for other eye characteristics (e.g., od_sph, os_cyl, os_axis, os_ucva, etc.) of the first patient as of Jun. 24, 2014. Interpolation/extrapolation module 103 can compare interpolated values for the other eye characteristic (of the first patient) to values for the other eye characteristics recorded for the Jun. 24, 2014 examination (for the second patient). If values recorded for the Jun. 24, 2014 examination are within a specified range of the interpolated values, interpolation/extrapolation module 103 considers eye characteristics of the second patient to have requisite correlation with eye characteristics of the first patient. Interpolation/extrapolation module 103 can then use os_sph values from the first patient to interpolate an estimated os_sph value of 1.5 for the second patient at the Jun. 24, 2014 examination.

In other aspects, interpolation/extrapolation module 103 use values for a plurality of patients to interpolate and/or extrapolate missing values for another patient.

Interpolation/Extrapolation module 103 outputs filled-in examination data 132. Filled-in examination data 132 includes sorted examination 131 with a number of (and potentially all) missing values in examination data 109 replaced with interpolated and/or extrapolated values. Outlier removal module 104 receives filled-in examination data 132 as input.

Outlier removal module 104 identifies and removes any outliers from filled-in examination data 132 (including outliers placed in examination data through interpolation and/or extrapolation). Outliers include values above and/or below specified thresholds as well as values that change to quickly over time. For example, outlier removal module 104 can identify and remove any values for cylinder (e.g., od_cyl or os_cyl) that are greater than 16. Outlier removal module 104 can also identify and remove any values for sphere (e.g., od_sph or os_sph) that increase by more than 0.5 per month.

In one aspect, outlier removal module 104 removes any outlying values within eye characteristic data for an examination but leaves other values for the examination intact. In another aspect, outlier removal module 104 removes all data for an examination if the examination includes any outlying values. In a further aspect, outlier removal module 104 removes all data for an examination if the examination includes a requisite number of (e.g., 2 or more) outlying values.

Outlier removal module outputs outlier removed examination data 133. Outlier removed examination data 133 includes filled-in examination data 132 with outlying values (either originally included in examination data 109 or added through interpolation/extrapolation) removed. Training data creator 106 receives outlier removed examination data 133 as input. Outlier removed examination data 133 is essentially sorted examination data with missing values replaced and outlying values removed.

Training data creator 106 uses outlier removed examination data 133 to create training data 134. Training data 134 can include different forms and types of training data used to train different types of regression models. In one aspect, for any two examinations for a single patient, a training data entry is formed from measured values for a first examination plus the time gap in months between the first examination and a second examination. A (e.g., sphere, cylinder, axis, etc.) value (for each eye) for the second examination is used as the label. As such, there can two labels per instances of training data, a (e.g., sphere, cylinder, axis, etc.) value for the left eye and (a e.g., sphere, cylinder, axis, etc.) value for the right eye.

Training data creator 106 outputs training data 134 including a plurality of training data entries. Model training module 107 receives training data 134 as input. Model training module 107 can use training data 134 to train on multiple regression models, such as, for example, FastTree, FastRank (boosted decision trees), Poisson, neural network based regression, etc. Models can be compared to one another to identify predictive model 136 (e.g., boosted decision trees based regression) that more appropriately forecasts changes in eye conditions (e.g., sphere, cylinder, eye conditions with a sphere component and a cylinder component, eye disease, etc.) over time. Model training module 107 can output predictive model 136.

Eye practitioners can use predictive model 136 to automatically forecast changes to eye conditions over time for eye patients. Predictive model 136 can be offered to eye practitioners as a Web API, as an application on the web, as a SaaS offering, as an application on mobiles, or any number of other platforms.

Figure 2:
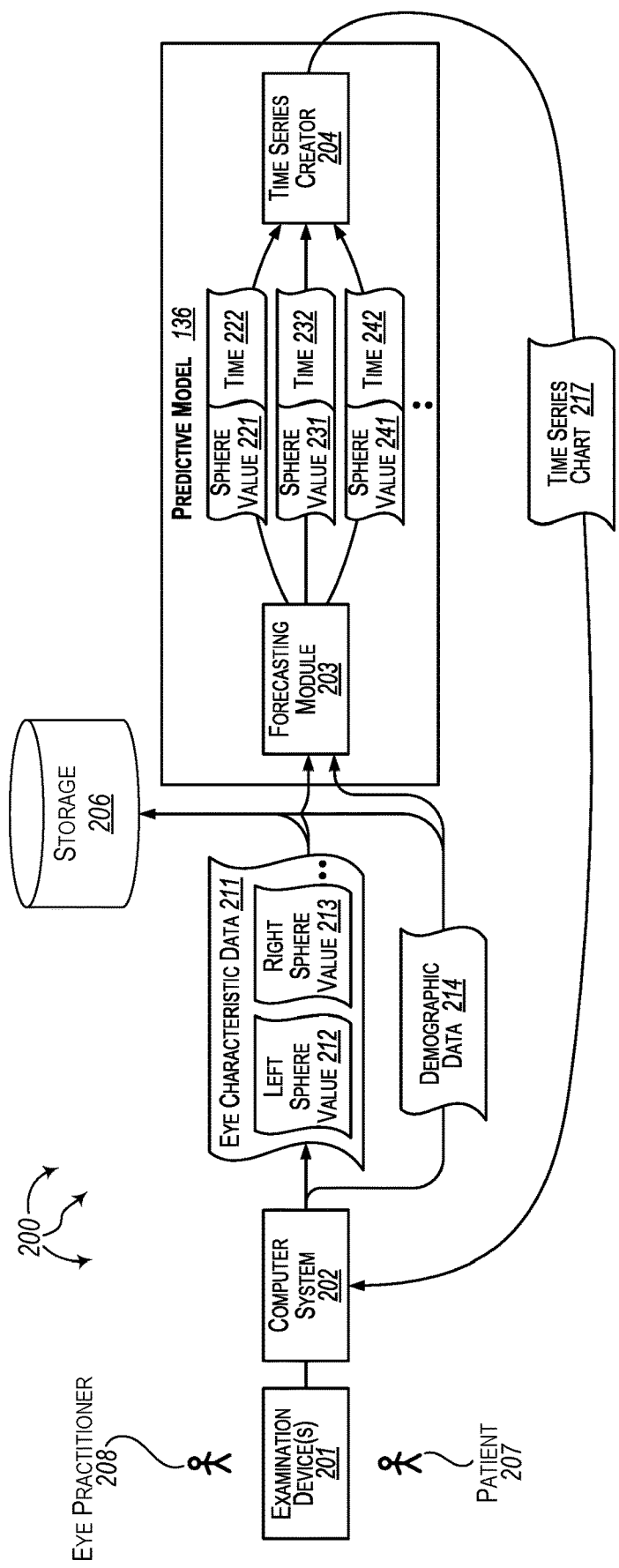
FIG. 2 illustrates an example computer architecture that facilitates forecasting sphere values for an eye patient.

Turning to FIG. 2, FIG. 2 illustrates an example computer architecture 200 that facilitates forecasting sphere values for an eye patient. Referring to FIG. 2, computer architecture 200 includes examination device(s) 201, computer system 202, storage 206, and predictive model 136. Examination device(s) 201, computer system 202, storage 206, and predictive model 136 can be connected to (or be part of) a network, such as, for example, a system bus, a Local Area Network ("LAN"), a Wide Area Network ("WAN"), and even the Internet. Accordingly, examination device(s) 201, computer system 202, storage 206, and predictive model 136 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Predictive model 136 can be run in system memory, such as, for example, system memory of computer system 202 or system memory within cloud resources.

Eye practitioner 208 can use examination device(s) 201 to measure and record values for eye characteristics of patient 207 (e.g., a pediatric patient). Examination device(s) 201 can (e.g., automatically) send measured values for eye characteristics of patient 207 to computer system 202. Values for various eye characteristics of patient 207 (UCVA, BVCA, sphere, cylinder, axis, etc.) can be included in eye characteristic data 211, including left sphere value 212 and right sphere value 213.

In one aspect, device(s) 201 include a device for generating a topographical map of patient 207's eyes. Eye characteristic data 211 can be derived at least in part from the topographical map. Demographic data for patient 207 (e.g., age, gender, location, etc.) can be recorded in demographic data 214 at computer system 202. Eye characteristic data 211 and demographic data 214 can be stored in storage 206 (which may be local at eye practitioner 208's office, at a remote storage location, in the cloud, etc.).

FIG. 3 illustrates a flow chart of an example method 300 for providing forecasting sphere values for an eye patient.

Method 300 will be described with respect to the components and data of computer architecture 200.

Method 300 includes accessing eye characteristic data for the patient's eyes, the eye characteristic data acquired during an eye examination performed on the patient, the eye characteristic data including one or more measured sphere values for the sphere of the patient's eyes (301). For example, predictive model 136 can access eye characteristic data 211, including left sphere value 212 and right sphere value 213. Method 300 includes accessing demographic data for the patient (302). For example, predictive model 136 can access demographic data 214.

Predictive model 136 can access each of eye characteristic data 211 and demographic data 214 from computer system 202 and/or from storage 206.

Method 300 includes inputting the eye characteristic data, including the one or more measured sphere values for the sphere of the patient's eyes, and the demographic data into a predictive model in the system memory, the predictive model formulated from other patient data acquired during other eye examinations for a plurality of other patients, the other patient data including, for each other patient included in the plurality of other patients, one or more measured sphere values for the sphere of the other patient's eyes, other eye characteristic data for the other patient's eyes, and demographic data for the other patient, the predictive model transforming the eye characteristic data for the patient, the demographic data for the patient, and the other patient data through linear regression (303). For example, eye characteristic data 211, including left sphere value 212 and right sphere value 213, and demographic data 214 can be input to forecasting module 203.

Transforming the eye characteristic data for the patient, the demographic data for the patient, and the other patient data through linear regression includes forecasting sphere values for the sphere of the patient's eyes at a plurality of different post examination time periods, the forecast sphere values inferred from the eye characteristic data for the patient, including the one or more measured sphere values for the sphere of the patient's eyes, and the demographic data for the patient in view of the other patient data (304). For example, forecasting module 203 can forecast od_sph and os_sph for patient 207 at a plurality of different time periods (e.g., one month, three months, six months, one year, two years, etc.) after the examination by eye practitioner 208.

Forecasting module 203 can forecast that patient 207 is to have sphere value 221 (e.g., a left or right sphere value) at time 222, can forecast that patient 207 is to have sphere value 231 (e.g., a left or right sphere value) at time 232, can forecast that patient 207 is to have sphere value 241 (e.g., a left or right sphere value) at time 242, etc. Sphere values 221, 231, 241, etc. can be inferred (e.g., interpolated and/or extrapolated) from left sphere value 212, right sphere value 213, and demographic data 214 in view of examination data 109 used to formulate predictive model 136.

Forecasting module 203 can output sphere value 221/time 222, sphere value 231/time 232, sphere value 241/time 242, etc. Time series creator 204 can receive sphere value 221/time 222, sphere value 231/time 232, sphere value 241/time 242, etc. as input.

Transforming the eye characteristic data for the patient, the demographic data for the patient, and the other patient data through linear regression includes formulating a time series chart of sphere for the patient's eyes from the forecast sphere values, the time series chart forecasting likely sphere values for the sphere of the patient's eyes over a plurality of different time periods in the future (305). For example, time series creator 204 can formulate time series chart 217 from sphere value 221/time 222, sphere value 231/time 232, sphere value 241/time 242, etc. Time series chart 217 forecasts likely sphere values for patient 207's eyes if no intervention is taken. Time series chart 217 can forecast that patient 207's eyes are likely to have sphere values 221, 222, 223, etc. over a plurality of different time periods (e.g., one month, three months, six months, one year, two years, etc.) in the future (e.g., as patient 207 ages).

In one aspect, time series chart 217 indicates likely sphere values for patient 207's eyes at six months, one year, and two years in the future. In another aspect, time series chart 217 indicates likely sphere values for patient 207's eyes every quarter for the next two years.

Method 300 includes returning the formulated time series chart as a prediction of changes to the sphere of the patient's eyes as the patient ages (306). For example, predictive model 136 can return time series chart 217 to computer system 202. Computer system 202 can present time series chart 217 at a user-interface screen. Eye practitioner 208 and patient 207 can view time series chart 217 at the user-interface screen. A hard copy of time series chart 217 can also be printed for eye practitioner 208 and/or patient 207.

Time series chart 217 can be used to assist eye practitioner 208 in tailoring a treatment plan for patient 207 and/or tailoring a subsequent examination schedule for patient 207. For example, if sphere is predicted to go very high for patient 207, eye practitioner 208 can recommend special care in terms of specific treatment or diet change or habit changes.

In one aspect, predictive model 136 tailors a treatment plan and/or an examination schedule plan for patient 207 based on time series chart 217. Predictive model 136 can return the tailored treatment plan and/or the tailored examination schedule to computer system 202 along with time series chart 217.

In another aspect, examination device(s) 201, computer system 202, and predictive model 136 operate in essentially real-time to provide time series chart 217. Data from examination device(s) 201 are automatically fed into computer system 202. In turn, computer system 202 automatically sends eye characteristic data 211 and demographic data 214 to predictive model 136. Predictive model 136 automatically generates and returns time series chart 217 back to computer system 202. Computer system 202 then automatically displays/prints time series chart 217.

In a further aspect, eye characteristic data 211 and demographic data 214 are provided as feedback to model formulation module 106 and/or are included in examination data 109. Eye characteristic data 211 and demographic data 214 can be used to facilitate further training and refinement of predictive model 136.

Computer architecture 200 and method 300 are advantageous to predict sphere for a patient having limited historical examination data (e.g., when a patient is undergoing a first eye exam or when data from previously eye practitioners is not available). In other aspects, examination data for two or more eye examinations for a patient may be available.

Figure 4:
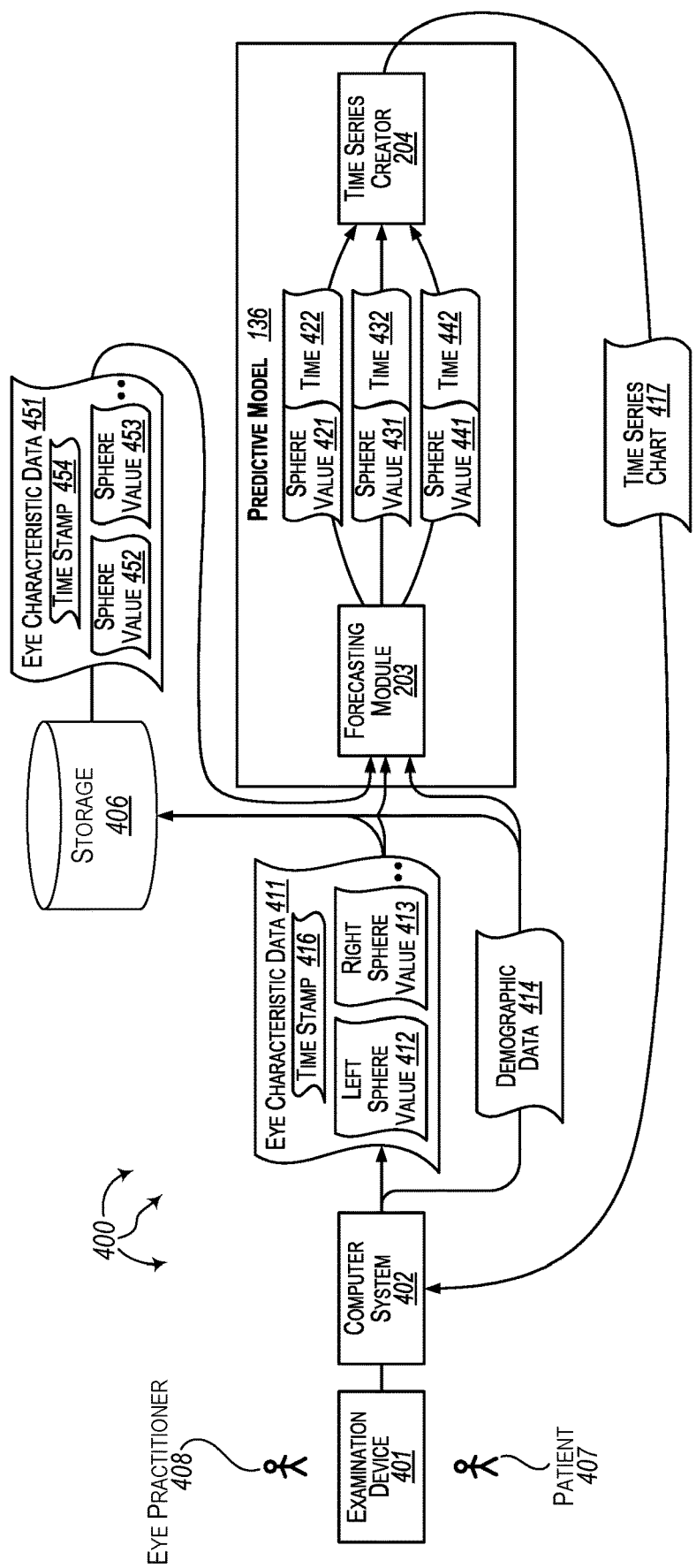
FIG. 4 illustrates an example computer architecture that facilitates forecasting sphere values for an eye patient.

FIG. 4 illustrates an example computer architecture 400 that facilitates forecasting sphere values for an eye patient. Referring to FIG. 4, computer architecture 400 includes examination device(s) 401, computer system 402, storage 406, and predictive model 136. Examination device(s) 401, computer system 402, storage 406, and predictive model 136 can be connected to (or be part of) a network, such as, for example, a system bus, a Local Area Network ("LAN"), a Wide Area Network ("WAN"), and even the Internet. Accordingly, examination device(s) 401, computer system 402, storage 406, and predictive model 136 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Predictive model 136 can be run in system memory, such as, for example, system memory of computer system 402 or system memory within cloud resources.

In one aspect, device(s) 401 include a device for generating a topographical map of patient 407's eyes. Eye characteristic data 411 can be derived at least in part from the topographical map. Demographic data for patient 407 (e.g., age, gender, location, etc.) can also be recorded in demographic data 414 at computer system 402.

Eye characteristic data 411 and demographic data 414 can be stored in storage 406 (which may be local at eye practitioner 408's office, at a remote storage location, in the cloud, etc.). Eye characteristic data from patient 407's prior eye examinations, such as, for example, eye characteristic data 451, can also be stored in storage 406.

FIG. 5 illustrates a flow chart of an example method 500 for forecasting sphere values for an eye patient. Method 500 will be described with respect to the components and data of computer architecture 400.

Method 500 includes accessing eye characteristic data for the patient's eyes, the eye characteristic data acquired during a plurality of different eye examinations performed on the patient, each eye examination included in the plurality of different eye examinations performed at a different time and separated from a next subsequent eye exam included in the plurality of eye different eye examinations by a time gap, for each of the plurality of different eye examinations, the eye characteristic data including one or more measured sphere values for the sphere of the patient's eyes (501). For example, predictive model 136 can access eye characteristic data 411 and eye characteristic data 451. Comparing time stamp 416 and time stamp 456 indicates a time gap 471 (e.g., in months or years) between the time of eye practitioner 408's current examination of patient 407 and the time when eye characteristic data 451 was measured during a prior examination of patient 407's eyes. As depicted, eye characteristic data 411 includes left sphere value 412 and right sphere value 413 and eye characteristic data 451 includes left sphere value 452 and right sphere value 453.

Method 500 includes accessing demographic data for the patient (502). For example, predictive model 136 can access demographic data 414.

Predictive model 136 can access each of eye characteristic data 411, eye characteristic data 451, and demographic data 414 from computer system 402 and/or from storage 406.

Method 500 includes inputting the eye characteristic data, time gaps, and demographic data into a predictive model, the eye characteristic data including, for each of the plurality of different eye examinations, the one or more measured sphere values for the sphere of the patient's eyes, the predictive model formulated from other patient data acquired during other eye examinations for a plurality of other patients, the other patient data including, for each other patient included in the plurality of other patients, one or more measured sphere values for the sphere of the other patient's eyes, other eye characteristic data for the other patient's eyes, and demographic data for the other patient, the predictive model transforming the eye characteristic data for the patient, the time gaps, and the demographic data for the patient through linear regression (503).

For example, eye characteristic data 411, including left sphere value 412 and right sphere value 413, eye characteristic data 451, including left sphere value 452 and right sphere value 453, and demographic data 414 can be input to forecasting module 203. Forecasting module 203 can calculate time gap 471 by comparing time stamp 456 and to time stamp 416.

Transforming the eye characteristic data for the patient, the time gaps, and the demographic data for the patient through linear regression includes forecasting sphere values for the sphere of the patient's eyes at a plurality of different post examination time periods, the forecast sphere values inferred from the one or more measured sphere values for the sphere of the patient's eyes acquired during different eye examinations for the patient and from the demographic data for the patient in view of the time gaps separating each of the plurality of eye examinations (504). For example, forecasting module 203 can forecast od_sph and os_sph for patient 407 at a plurality of different time periods (e.g., one month, three months, six months, one year, two years, etc.) after the examination by eye practitioner 408.

Forecasting module 203 can forecast that patient 407 is to have sphere value 421 (e.g., a left or right sphere value) at time 422, can forecast that patient 407 is to have sphere value 431 (e.g., a left or right sphere value) at time 432, can forecast that patient 407 is to have sphere value 441 (e.g., a left or right sphere value) at time 442, etc. Sphere values 421, 431, 441, etc. can be inferred (e.g., interpolated and/or extrapolated) from left sphere value 412, right sphere value 413, left sphere value 452, right sphere value 453, and demographic data 414 in view of time gap 471.

Forecasting module 203 can output sphere value 421/time 422, sphere value 431/time 432, sphere value 441/time 442, etc. Time series creator 204 can receive sphere value 421/time 422, sphere value 431/time 432, sphere value 441/time 442, etc. as input.

Transforming the eye characteristic data for the patient, the time gaps, and the demographic data for the patient through linear regression includes formulating a time series chart of sphere for the patient's eyes from the forecast sphere values, the time series chart forecasting likely sphere values for the sphere of the patient's eyes over a plurality of different time periods in the future (505). For example, time series creator 204 can formulate time series chart 417 from sphere value 421/time 422, sphere value 431/time 432, sphere value 441/time 442, etc. Time series chart 417 forecasts likely sphere values for patient 407's eyes if no intervention is taken. Time series chart 417 can forecast that patient 407's eyes are likely to have sphere values 421, 422, 423, etc. over a plurality of different time periods (e.g., one month, three months, six months, one year, two years, etc.) in the future (e.g., as patient 407 ages).

In one aspect, time series chart 417 indicates likely sphere values for patient 407's eyes at six months, one year, and two years in the future. In another aspect, time series chart 417 indicates likely sphere values for patient 407's eyes every quarter for the next two years.

Method 500 includes returning the formulated time series chart as a prediction of changes to the sphere of the patient's eyes as the patient ages (506). For example, predictive model 136 can return time series chart 417 to computer system 402. Computer system 402 can present time series chart 417 at a user-interface screen. Eye practitioner 408 and patient 407 can view time series chart 417 at a user-interface screen. A hard copy of time series chart 417 can also be printed for eye practitioner 408 and/or patient 407.

Time series chart 417 can be used to assist eye practitioner 408 in tailoring a treatment plan and/or tailoring a subsequent examination schedule for patient 407. For example, if sphere is predicted to go very high for patient 407, eye practitioner 408 can recommend special care in terms of specific treatment or diet change or habit changes.

In one aspect, predictive model 136 tailors a treatment plan and/or an examination schedule for the patient based on time series chart 417. Predictive model 136 can return the tailored treatment plan and/or the tailored examination schedule to computer system 402 along with time series chart 417.

In another aspect, examination device(s) 401, computer system 402, storage 406, and predictive model 436 operate in essentially real-time to provide time series chart 417. Data from examination device(s) 401 are automatically fed into computer system 402. In turn, computer system 402 automatically sends eye characteristic data 411 and demographic data 414 to predictive model 136. Computer system 402 also automatically instructs storage 406 to send eye characteristic data 451 to predictive model 136. Predictive model 136 automatically generates and returns time series chart 417 back to computer system 402. Computer system 402 then automatically displays/prints time series chart 417.

In a further aspect, eye characteristic data 411 and demographic data 414 are provided as feedback to model formulation module 106 and/or are included in examination data 109. Eye characteristic data 411 and demographic data 414 can be used to facilitate further training and refinement of predictive model 136.

Accordingly, aspects of the invention can be used to forecast eye sphere for a patient (e.g., a pediatric patient) given a current eye examination and demographic details. Regression models can be used to effectively forecast eye sphere based on demographics and eye examination features. Other machine learning methods and other forms of classification and regression can also be used.

FIGS. 2-5 primarily describe using a predictive model to predict changes in sphere. In other aspects, a predictive model can be used to predict changes in other eye conditions, such as, for example, cylinder, eye conditions having both a sphere component and a cylinder component (e.g., sphere+cylinder/2), eye conditions based on other described eye characteristics, eye diseases, etc. Returning briefly to FIG. 1, predictive model 136 can also be trained from examination data 109 to predict changes to any of: cylinder, an eye condition having a sphere component and a cylinder component, an eye condition based on other described eye characteristics, an eye disease, etc.

Figure 6:
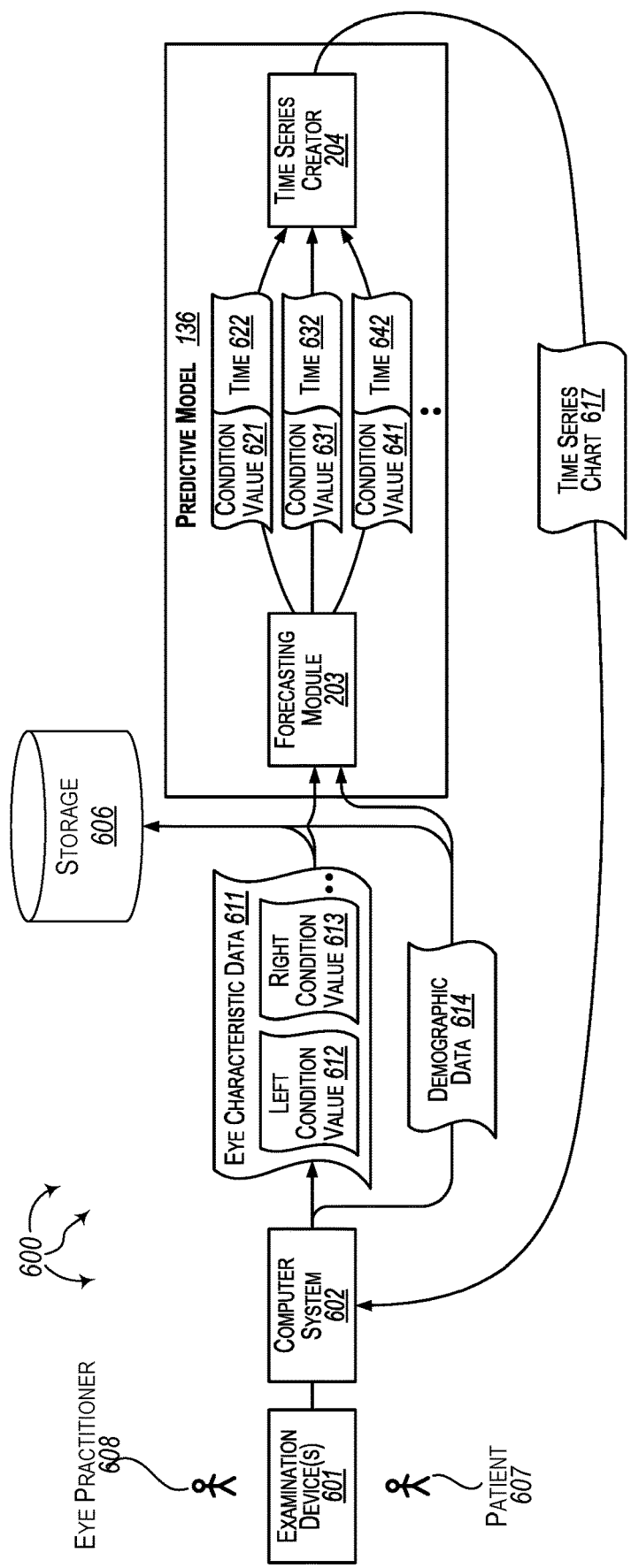
FIG. 6 illustrates an example computer architecture that facilitates forecasting progression of an eye condition for an eye patient.

FIG. 6 illustrates an example computer architecture 600 that facilitates forecasting progression of an eye condition for an eye patient. Referring to FIG. 6, computer architecture 600 includes examination device(s) 601, computer system 602, storage 606, and predictive model 136. Examination device(s) 601, computer system 602, storage 606, and predictive model 136 can be connected to (or be part of) a network, such as, for example, a system bus, a Local Area Network ("LAN"), a Wide Area Network ("WAN"), and even the Internet. Accordingly, examination device(s) 601, computer system 602, storage 606, and predictive model 136 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Predictive model 136 can be run in system memory, such as, for example, system memory of computer system 602 or system memory within cloud resources.

Eye practitioner 608 can use examination device(s) 601 to measure and record values for eye characteristics of patient 607 (e.g., a pediatric patient). Examination device(s) 601 can (e.g., automatically) send measured values for eye characteristics of patient 607 to computer system 602. Values for various eye characteristics of patient 607 (UCVA, BVCA, sphere, cylinder, axis, etc.) can be included in eye characteristic data 611, including left condition value 612 and right condition value 613.

In one aspect, device(s) 601 include a device for generating a topographical map of patient 607's eyes. Eye characteristic data 611 can be derived at least in part from the topographical map. Demographic data for patient 607 (e.g., age, gender, location, etc.) can be recorded in demographic data 614 at computer system 602. Eye characteristic data 611 and demographic data 614 can be stored in storage 606 (which may be local at eye practitioner 608's office, at a remote storage location, in the cloud, etc.).

Predictive model 136 can access eye characteristic data 611, including left condition value 612 and right condition value 613. A condition value can be a value for an eye condition, such as, for example, sphere, cylinder, a condition with a sphere component and a cylinder component (e.g., sphere+cylinder/2), a condition based on other described eye characteristics, an eye disease, etc. Predictive model 136 can also access demographic data 614. Predictive model 136 can access each of eye characteristic data 611 and demographic data 614 from computer system 602 and/or from storage 606.

Eye characteristic data 611, including left condition value 612 and right condition value 613, and demographic data 614 can be input to forecasting module 203. Forecasting module 203 can forecast values for the left eye condition and the right eye condition for patient 207 at a plurality of different time periods (e.g., one month, three months, six months, one year, two years, etc.) after the examination by eye practitioner 208.

Forecasting module 203 can forecast that patient 607 is to have condition value 221 (e.g., a left or right condition value) at time 622, can forecast that patient 607 is to have condition value 631 (e.g., a left or right condition value) at time 632, can forecast that patient 607 is to have condition value 641 (e.g., a left or right condition value) at time 642, etc. Condition values 621, 631, 641, etc. can be inferred (e.g., interpolated and/or extrapolated) from left condition value 612, right condition value 613, and demographic data 614 in view of examination data 109 used to formulate predictive model 136.

Forecasting module 203 can output condition value 621/time 622, condition value 631/time 632, condition value 641/time 642, etc. Time series creator 204 can receive condition value 621/time 622, condition value 631/time 632, condition value 641/time 642, etc. as input.

Time series creator 204 can formulate time series chart 217 from condition value 621/time 622, condition value 631/time 632, condition value 641/time 642, etc. Time series chart 617 forecasts likely condition values for patient 607's eyes if no intervention is taken. Time series chart 617 can forecast that patient 607's eyes are likely to have condition values 621, 622, 623, etc. over a plurality of different time periods (e.g., one month, three months, six months, one year, two years, etc.) in the future (e.g., as patient 607 ages).

In one aspect, time series chart 617 indicates likely condition values for patient 607's eyes at six months, one year, and two years in the future. In another aspect, time series chart 617 indicates likely condition values for patient 607's eyes every quarter for the next two years.

Predictive model 136 can return time series chart 617 to computer system 602. Computer system 602 can present time series chart 617 at a user-interface screen. Eye practitioner 608 and patient 607 can view time series chart 617 at the user-interface screen. A hard copy of time series chart 617 can also be printed for eye practitioner 608 and/or patient 607.

Time series chart 617 can be used to assist eye practitioner 608 in tailoring a treatment plan for patient 607 and/or tailoring a subsequent examination schedule for patient 607. For example, if cylinder is predicted to go very high for patient 607, eye practitioner 608 can recommend special care in terms of specific treatment or diet change or habit changes.

In one aspect, predictive model 136 tailors a treatment plan and/or an examination schedule plan for patient 607 based on time series chart 617. Predictive model 136 can return the tailored treatment plan and/or the tailored examination schedule to computer system 602 along with time series chart 617.

In another aspect, examination device(s) 601, computer system 602, and predictive model 136 operate in essentially real-time to provide time series chart 617. Data from examination device(s) 601 are automatically fed into computer system 602. In turn, computer system 602 automatically sends eye characteristic data 611 and demographic data 614 to predictive model 136. Predictive model 136 automatically generates and returns time series chart 617 back to computer system 602. Computer system 602 then automatically displays/prints time series chart 617.

In a further aspect, eye characteristic data 611 and demographic data 614 are provided as feedback to model formulation module 106 and/or are included in examination data 109. Eye characteristic data 611 and demographic data 614 can be used to facilitate further training and refinement of predictive model 136.

Computer architecture 600 and is advantageous to predict progression of eye conditions for a patient having limited historical examination data (e.g., when a patient is undergoing a first eye exam or when data from previously eye practitioners is not available). In other aspects, examination data for two or more eye examinations for a patient may be available.

Figure 7:
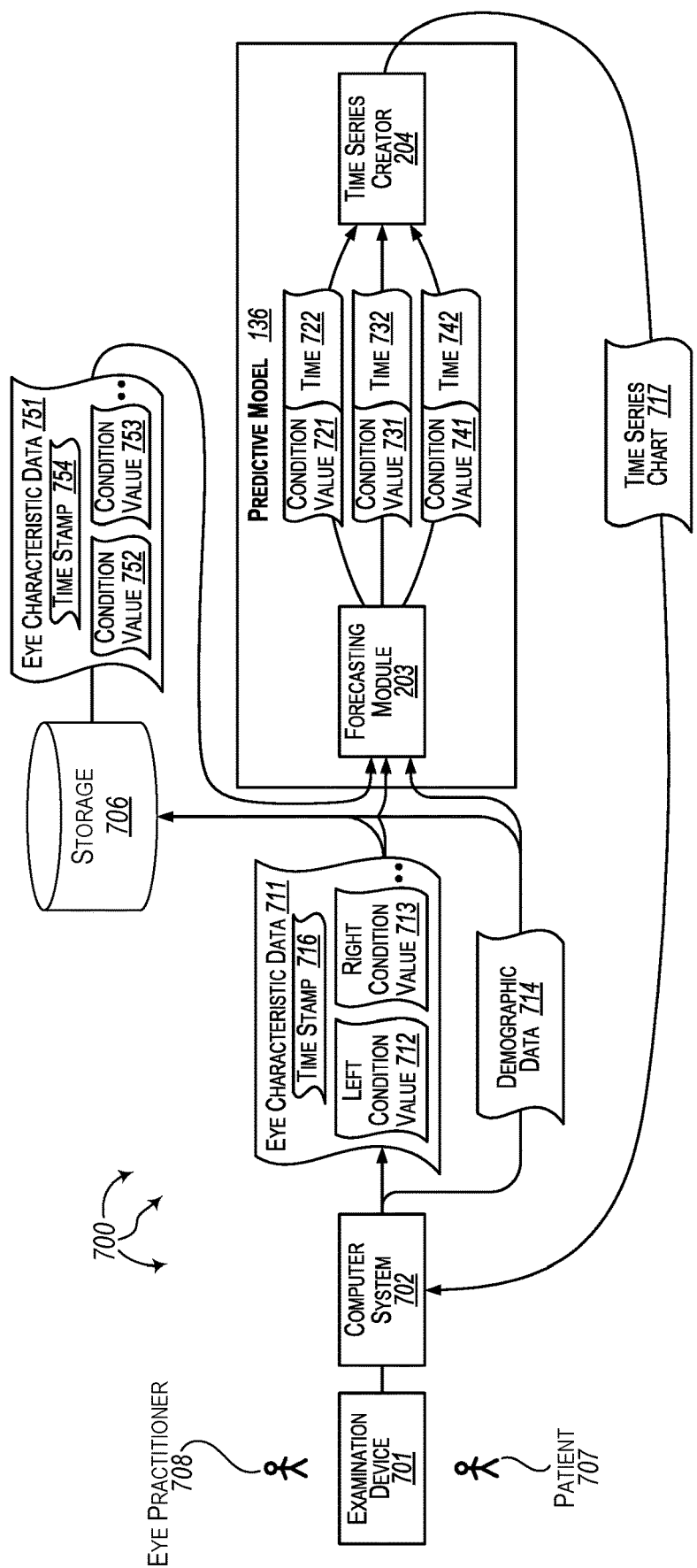
FIG. 7 illustrates an example computer architecture that facilitates forecasting progression of an eye condition for an eye patient.

FIG. 7 illustrates an example computer architecture 700 that facilitates forecasting progression of an eye condition for an eye patient. Referring to FIG. 7, computer architecture 700 includes examination device(s) 701, computer system 702, storage 706, and predictive model 136. Examination device(s) 701, computer system 702, storage 706, and predictive model 136 can be connected to (or be part of) a network, such as, for example, a system bus, a Local Area Network ("LAN"), a Wide Area Network ("WAN"), and even the Internet. Accordingly, examination device(s) 701, computer system 702, storage 706, and predictive model 136 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

Predictive model 136 can be run in system memory, such as, for example, system memory of computer system 702 or system memory within cloud resources.

In one aspect, device(s) 701 include a device for generating a topographical map of patient 707's eyes. Eye characteristic data 711 can be derived at least in part from the topographical map. Demographic data for patient 707 (e.g., age, gender, location, etc.) can also be recorded in demographic data 714 at computer system 702.

Eye characteristic data 711 and demographic data 714 can be stored in storage 706 (which may be local at eye practitioner 708's office, at a remote storage location, in the cloud, etc.). Eye characteristic data from patient 707's prior eye examinations, such as, for example, eye characteristic data 751, can also be stored in storage 706.

Predictive model 136 can access eye characteristic data 711 and eye characteristic data 751. Comparing time stamp 716 and time stamp 756 indicates a time gap 771 (e.g., in months or years) between the time of eye practitioner 708's current examination of patient 707 and the time when eye characteristic data 751 was measured during a prior examination of patient 707's eyes. As depicted, eye characteristic data 711 includes left condition value 712 and right condition value 713 and eye characteristic data 751 includes left condition value 752 and right condition value 753. A condition value can be a value for an eye condition, such as, for example, sphere, cylinder, a condition with a sphere component and a cylinder component (e.g., sphere+cylinder/2), a condition based on other described eye characteristics, an eye disease, etc. Predictive model 136 can also access demographic data 714. Predictive model 136 can access each of eye characteristic data 711, eye characteristic data 751, and demographic data 714 from computer system 702 and/or from storage 706.

Eye characteristic data 711, including left condition value 712 and right condition value 713, eye characteristic data 751, including left condition value 752 and right condition value 753, and demographic data 714 can be input to forecasting module 203. Forecasting module 203 can calculate time gap 771 by comparing time stamp 756 and to time stamp 716.

Forecasting module 203 can forecast a left condition value and a right condition value for patient 707 at a plurality of different time periods (e.g., one month, three months, six months, one year, two years, etc.) after the examination by eye practitioner 708.

Forecasting module 203 can forecast that patient 707 is to have condition value 721 (e.g., a left or right eye disease value) at time 722, can forecast that patient 707 is to have condition value 731 (e.g., a left or right disease value) at time 732, can forecast that patient 707 is to have condition value 741 (e.g., a left or right disease value) at time 742, etc. Condition values 721, 731, 741, etc. can be inferred (e.g., interpolated and/or extrapolated) from left condition value 712, right condition value 713, left condition value 752, right condition value 753, and demographic data 714 in view of time gap 771.

Forecasting module 203 can output condition value 721/time 722, condition value 731/time 732, condition value 741/time 742, etc. Time series creator 204 can receive condition value 721/time 722, condition value 731/time 732, condition value 741/time 742, etc. as input.

Time series creator 204 can formulate time series chart 717 from condition value 721/time 722, condition value 731/time 732, condition value 741/time 742, etc. Time series chart 717 forecasts likely condition values for patient 707's eyes if no intervention is taken. Time series chart 717 can forecast that patient 707's eyes are likely to have condition values 721, 722, 723, etc. over a plurality of different time periods (e.g., one month, three months, six months, one year, two years, etc.) in the future (e.g., as patient 707 ages).

In one aspect, time series chart 717 indicates likely condition values for patient 707's eyes at six months, one year, and two years in the future. In another aspect, time series chart 717 indicates likely condition values for patient 707's eyes every quarter for the next two years.

For example, predictive model 136 can return time series chart 717 to computer system 702. Computer system 702 can present time series chart 717 at a user-interface screen. Eye practitioner 708 and patient 707 can view time series chart 717 at a user-interface screen. A hard copy of time series chart 717 can also be printed for eye practitioner 708 and/or patient 707.

Time series chart 717 can be used to assist eye practitioner 708 in tailoring a treatment plan and/or tailoring a subsequent examination schedule for patient 707. For example, if an eye condition is expected to worsen for patient 707, eye practitioner 708 can recommend special care in terms of specific treatment or diet change or habit changes.

In one aspect, predictive model 136 tailors a treatment plan and/or an examination schedule for the patient based on time series chart 717. Predictive model 136 can return the tailored treatment plan and/or the tailored examination schedule to computer system 702 along with time series chart 717.

In another aspect, examination device(s) 701, computer system 702, storage 706, and predictive model 736 operate in essentially real-time to provide time series chart 717. Data from examination device(s) 701 are automatically fed into computer system 702. In turn, computer system 702 automatically sends eye characteristic data 711 and demographic data 714 to predictive model 136. Computer system 702 also automatically instructs storage 706 to send eye characteristic data 751 to predictive model 136. Predictive model 136 automatically generates and returns time series chart 717 back to computer system 702. Computer system 702 then automatically displays/prints time series chart 717.

In a further aspect, eye characteristic data 711 and demographic data 714 are provided as feedback to model formulation module 106 and/or are included in examination data 109. Eye characteristic data 711 and demographic data 714 can be used to facilitate further training and refinement of predictive model 136.

Accordingly, aspects of the invention can be used to forecast eye conditions for a patient (e.g., a pediatric patient) given a current eye examination and demographic details. Regression models can be used to effectively forecast eye conditions based on demographics and eye examination features. Other machine learning methods and other forms of classification and regression can also be used.

In some aspects, a computer system comprises one or more hardware processors and system memory. The one or more hardware processors are configured to execute instructions stored in the system memory to automatically predict progression of an eye condition for a patient's eyes. An eye condition can include, for example, sphere, cylinder, a condition with a sphere component and a cylinder component, a condition based on other described eye characteristics, an eye disease, etc.

The one or more hardware processors execute instructions stored in the system memory to access eye characteristic data for the patient's eyes. The eye characteristic data is acquired during an eye examination performed on the patient. The eye characteristic data includes one or more measured condition values for the eye condition of the patient's eyes. The one or more hardware processors execute instructions stored in the system memory to access demographic data for the patient.

The one or more hardware processors execute instructions stored in the system memory to input the eye characteristic data, including the one or more measured condition values for the eye condition of the patient's eyes, and the demographic data into a predictive model in the system memory. The predictive model having been formulated from other patient data acquired during other eye examinations for a plurality of other patients. The other patient data includes, for each other patient included in the plurality of other patients, one or more measured condition values for the eye condition of the other patient's eyes, other eye characteristic data for the other patient's eyes, and demographic data for the other patient. The predictive model is configured to transform the eye characteristic data for the patient, the demographic data for the patient, and the other patient data through linear regression.

The one or more hardware processors execute instructions stored in the system memory to forecast condition values for the eye condition of the patient's eyes at a plurality of different post examination time periods. The forecast condition values are inferred from the eye characteristic data for the patient, including the one or more measured condition values for the eye condition of the patient's eyes, and the demographic data for the patient in view of the other patient data.

The one or more hardware processors execute instructions stored in the system memory to formulate a time series chart of condition values for the patient's eyes from the forecast condition values. The time series chart forecasts likely condition values for the eye condition of the patient's eyes over a plurality of different time periods in the future. The one or more hardware processors execute instructions stored in the system memory to return the formulated time series chart as a prediction of changes to the eye condition of the patient's eyes in the future and/or as the patient ages.

In other aspects, a computer system comprises one or more hardware processors and system memory. The one or more hardware processors are configured to execute instructions stored in the system memory to automatically predict progression of an eye condition for a patient's eyes. An eye condition can include, for example, sphere, cylinder, a condition with a sphere component and a cylinder component, a condition based on other described eye characteristics, an eye disease, etc.

The one or more hardware processors execute instructions stored in the system memory to access eye characteristic data for the patient's eyes. The eye characteristic data having been acquired during a plurality of different eye examinations performed on the patient. Each eye examination included in the plurality of different eye examinations was performed at a different time and separated from a next subsequent eye exam included in the plurality of eye different eye examinations by a time gap. For each of the plurality of different eye examinations, the eye characteristic data includes one or more measured condition values for the eye condition of the patient's eyes. The one or more hardware processors execute instructions stored in the system memory to access demographic data for the patient.

The one or more hardware processors execute instructions stored in the system memory to input the eye characteristic data, time gaps, and demographic data into a predictive model. The eye characteristic data includes for each of the plurality of different eye examinations, the one or more measured condition values for the eye condition of the patient's eyes. The predictive model having been formulated from other patient data acquired during other eye examinations for a plurality of other patients. The other patient data includes, for each other patient included in the plurality of other patients, one or more measured condition values for the eye condition of the other patient's eyes, other eye characteristic data for the other patient's eyes, and demographic data for the other patient. The predictive model is configured to transform the eye characteristic data for the patient, the time gaps, and the demographic data for the patient through linear regression.

The one or more hardware processors execute instructions stored in the system memory to forecast condition values for the eye condition of the patient's eyes at a plurality of different post examination time periods. The forecast condition values inferred from the one or more measured condition values for the sphere of the patient's eyes acquired during different eye examinations for the patient and from the demographic data for the patient in view of the time gaps separating each of the plurality of eye examinations.

The one or more hardware processors execute instructions stored in the system memory to formulate a time series chart of the eye condition for the patient's eyes from the forecast condition values. The time series chart forecasts likely condition values for the eye condition of the patient's eyes over a plurality of different time periods in the future. The one or more hardware processors execute instructions stored in the system memory to return the formulated time series chart as a prediction of changes to the eye condition of the patient's eyes in the future and/or as the patient ages.

Computer implemented methods for performing the executed instructions to (e.g., automatically) predict progress of an eye condition for a patient's eyes are also contemplated. Computer program products storing the instructions, that when executed by a processor, cause a computer system to (e.g., automatically) predict progress of an eye condition for a patient's eyes are also contemplated.

The present described aspects may be implemented in other specific forms without departing from its spirit or essential characteristics. The described aspects are to be considered in all respects only as illustrative and not restrictive. The scope is, therefore, indicated by the appended claims rather than by the foregoing description. All changes which come within the meaning and range of equivalency of the claims are to be embraced within their scope.

What is claimed:

1. A computer system, the computer system comprising:
   one or more hardware processors;
   system memory coupled to the one or more hardware processors, the system memory storing instructions that are executable by the one or more hardware processors;
   the one or more hardware processors executing the instructions stored in the system memory to predict a sphere for a patient's eyes, including the following:
   access eye characteristic data for the patient's eyes, the eye characteristic data acquired during an eye examination performed on the patient, the eye characteristic data including one or more measured sphere values for the sphere of the patient's eyes;
   access demographic data for the patient;
   input the eye characteristic data, including the one or more measured sphere values for the sphere of the patient's eyes, and the demographic data into a predictive model in the system memory, the predictive model formulated from other patient data acquired during other eye examinations for a plurality of other patients, the other patient data including, for each other patient included in the plurality of other patients, one or more measured sphere values for the sphere of the other patient's eyes, other eye characteristic data for the other patient's eyes, and demographic data for the other patient, the predictive model transforming the eye characteristic data for the patient, the demographic data for the patient, and the other patient data through linear regression to:
   forecast sphere values for the sphere of the patient's eyes at a plurality of different post examination time periods, the forecast sphere values inferred from the eye characteristic data for the patient, including the one or more measured sphere values for the sphere of the patient's eyes, and the demographic data for the patient in view of the other patient data; and
   formulate a time series chart of sphere for the patient's eyes from the forecast sphere values, the time series chart forecasting likely sphere values for the sphere of the patient's eyes over a plurality of different time periods in the future; and
   output the formulated time series chart as a prediction of changes to the sphere of the patient's eyes as the patient ages.

2. The computer system of claim 1, wherein the one or more hardware processors executing the instructions stored in the system memory to access the eye characteristic data for the patient's eyes comprises the one or more hardware processors executing the instructions stored in the system memory to access one or more of: cylinder, axis, uncorrected visual acuity (UCVA), and best-corrected visual acuity (BCVA) for the patient.

3. The computer system of claim 1, wherein the one or more hardware processors executing the instructions stored in the system memory to access the eye characteristic data for the patient's eyes comprises the one or more hardware processors executing the instructions stored in the system memory to access results from a topological map of the patient's eyes.

4. The computer system of claim 1, wherein the one or more hardware processors executing the instructions stored in the system memory to return the formulated time series chart comprises the one or more hardware processors executing the instructions stored in the system memory to return a time series chart indicating predicted sphere for the patient's eyes at six months, one year, and two years after the eye examination.

5. The computer system of claim 1, wherein the one or more hardware processors executing the instructions stored in the system memory to access the eye characteristic data for the patient's eyes comprises the one or more hardware processors executing the instructions stored in the system memory to access the eye characteristic data for a pediatric patient.

6. The computer system of claim 1, wherein the one or more hardware processors executing the instructions stored in the system memory to transform the eye characteristic data for the patient, the demographic data for the patient, and the other patient data through linear regression comprises the one or more hardware processors executing the instructions stored in the system memory to transform the eye characteristic data for the patient, the demographic data for the patient, and the other patient data through one of:

gradient tree boosting regression, online gradient descent based regression, neural network based regression, or Poisson regression.

7. The computer system of claim 1, wherein the one or more hardware processors executing the instructions stored in the system memory to forecast sphere values for the sphere of the patient's eyes at the plurality of different post examination time periods comprises the one or more hardware processors executing the instructions stored in the system memory to forecast the sphere of the patient's eyes at the plurality of different post examination time periods based on sphere values for the sphere of one or more other patients, from among the plurality of other patients, having a specified similarity of demographic data to the demographic data of the patient.

8. The computer system of claim 1, further comprising the one or more hardware processors executing the instructions stored in the system memory to tailor an eye care plan for the patient based on the formulated time series chart.

9. A computer system, the computer system comprising:
one or more hardware processors;
system memory coupled to the one or more hardware processors, the system memory storing instructions that are executable by the one or more hardware processors;
the one or more hardware processors executing the instructions stored in the system memory to predict a sphere for a patient's eyes, including the following:
access eye characteristic data for the patient's eyes, the eye characteristic data acquired during a plurality of different eye examinations performed on the patient, each eye examination included in the plurality of different eye examinations performed at a different time and separated from a next subsequent eye exam included in the plurality of different eye examinations by a time gap, for each of the plurality of different eye examinations, the eye characteristic data including one or more measured sphere values for the sphere of the patient's eyes;
access demographic data for the patient;
input the eye characteristic data, time gaps, and the demographic data into a predictive model, the eye characteristic data including, for each of the plurality of different eye examinations, the one or more measured sphere values for the sphere of the patient's eyes, the predictive model formulated from other patient data acquired during other eye examinations for a plurality of other patients, the other patient data including, for each other patient included in the plurality of other patients, one or more measured sphere values for the sphere of the other patient's eyes, other eye characteristic data for the other patient's eyes, and demographic data for the other patient, the predictive model transforming the eye characteristic data for the patient, the time gaps, and the demographic data for the patient through linear regression to:
forecast sphere values for the sphere of the patient's eyes at a plurality of different post examination time periods, the forecast sphere values inferred from the one or more measured sphere values for the sphere of the patient's eyes acquired during different eye examinations for the patient and from the demographic data for the patient in view of the time gaps separating each of the plurality of different eye examinations; and
formulate a time series chart of sphere for the patient's eyes from the forecast sphere values, the time series chart forecasting likely sphere values for the sphere of the patient's eyes over a plurality of different time periods in the future; and
output the formulated time series chart as a prediction of changes to the sphere of the patient's eyes as the patient ages.

10. The computer system of claim 9, wherein the one or more hardware processors executing the instructions stored in the system memory to access the eye characteristic data for the patient's eyes comprises the one or more hardware processors executing the instructions stored in the system memory to access one or more of: cylinder, axis, uncorrected visual acuity (UCVA), and best-corrected visual acuity (BCVA) for the patient.

11. The computer system of claim 9, wherein the one or more hardware processors executing the instructions stored in the system memory to access the eye characteristic data for the patient's eyes comprises the one or more hardware processors executing the instructions stored in the system memory to access results from a topological map of the patient's eyes.

12. The computer system of claim 9, wherein the one or more hardware processors executing the instructions stored in the system memory to return the formulated time series chart comprises the one or more hardware processors executing the instructions stored in the system memory to return a time series chart indicating predicted sphere for the patient's eyes at six months, one year, and two years after the last eye examination included in the plurality of different eye examinations.

13. The computer system of claim 9, wherein the one or more hardware processors executing the instructions stored in the system memory to access the eye characteristic data for the patient's eyes comprises the one or more hardware processors executing the instructions stored in the system memory to access the eye characteristic data for a pediatric patient.

14. The computer system of claim 9, wherein the one or more hardware processors executing the instructions stored in the system memory to transform the eye characteristic data for the patient, the time gaps, and the demographic data for the patient through linear regression comprises the one or more hardware processors executing the instructions stored in the system memory to transform the eye characteristic data for the patient, the time gaps, and the demographic data for the patient through one of: gradient tree boosting regression, online gradient descent based regression, neural network based regression, or Poisson regression.

15. The computer system of claim 9, wherein the one or more hardware processors executing the instructions stored in the system memory to transform the eye characteristic data for the patient, the time gaps, and the demographic data for the patient through linear regression comprises the one or more hardware processors executing the instructions stored in the system memory to transform the eye characteristic data for the patient, the time gaps, the demographic data for the patient, and the other patient data through linear regression.

16. The computer system of claim 9, wherein the one or more hardware processors executing the instructions stored in the system memory to forecast sphere values for the sphere of the patient's eyes at the plurality of different post examination time periods comprises the one or more hardware processors executing the instructions stored in the system memory to forecast sphere of the patient's eyes at the plurality of different post examination time periods based on changes in measured sphere values acquired during different eye examinations separated by a time gap.

17. The computer system of claim 9, further comprising the one or more hardware processors executing the instructions stored in the system memory to tailor an eye care plan for the patient based on the formulated time series chart.

* * * * *